(12) United States Patent
Musa

(10) Patent No.: US 6,307,001 B1
(45) Date of Patent: Oct. 23, 2001

(54) CURABLE HYBRID ELECTRON DONOR COMPOUNDS CONTAINING VINYL ETHER

(75) Inventor: Osama M. Musa, Hillsborough, NJ (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/573,376

(22) Filed: May 18, 2000

(51) Int. Cl.$^7$ .................................................. C08G 18/04
(52) U.S. Cl. .............................. 528/44; 528/32; 528/45; 528/59; 528/272; 526/335; 568/606; 568/27; 568/28; 568/38; 568/308; 568/579; 558/254; 560/330; 564/17; 564/32; 564/47
(58) Field of Search .................... 528/32, 44, 45, 528/59, 272; 526/335; 568/606, 27, 28, 38, 308, 579; 560/330; 564/17, 32, 47

(56) References Cited

U.S. PATENT DOCUMENTS

| | | | |
|---|---|---|---|
| 4,486,582 | 12/1984 | Heffner, Jr. | 526/301 |
| 4,543,397 | 9/1985 | Woods et al. | 525/455 |
| 4,640,849 | 2/1987 | Woods et al. | 427/54.1 |
| 4,732,956 | 3/1988 | Woods et al. | 526/260 |
| 4,749,807 | 6/1988 | Lapin et al. | 560/91 |
| 4,751,273 | 6/1988 | Lapin et al. | 525/455 |
| 4,775,732 | 10/1988 | Lapin et al. | 528/49 |
| 5,019,629 | 5/1991 | Woods et al. | 525/312 |
| 5,084,490 | 1/1992 | McArdle et al. | 522/181 |
| 5,183,946 | 2/1993 | Liu et al. | 568/670 |
| 5,334,456 | 8/1994 | Noren et al. | 428/431 |
| 5,491,178 | 2/1996 | Swedo et al. | 522/74 |
| 5,514,727 | 5/1996 | Green et al. | 522/15 |
| 5,516,455 | 5/1996 | Jacobine et al. | 252/299.01 |
| 5,539,014 | 7/1996 | Swedo et al. | 522/91 |
| 5,633,411 | 5/1997 | Woods et al. | 568/654 |
| 5,708,129 | 1/1998 | Nguyen et al. | 528/362 |
| 5,789,757 | 8/1998 | Husson, Jr. et al. | 252/183.11 |
| 6,034,194 | 3/2000 | Dershem et al. | 526/262 |
| 6,034,195 | 3/2000 | Dershem et al. | 526/262 |

OTHER PUBLICATIONS

"Co–Polymerization of Maleimides and Vinyl Ethers: A Structural Study" by P. Kohli, A. B. Scranton, and G. J. Blanchard; *Macromolecules 1998, 31, 5681–5689*.

Primary Examiner—Robert Dawson
Assistant Examiner—Kuo-Liang Peng
(74) Attorney, Agent, or Firm—Jane E. Gennaro

(57) ABSTRACT

Hybrid electron donor compounds, suitable for use as adhesives or as components in adhesives, contain a carbon to carbon double bond attached to an aromatic ring and conjugated with the unsaturation in the aromatic ring and a vinyl ether moiety.

4 Claims, No Drawings

CURABLE HYBRID ELECTRON DONOR COMPOUNDS CONTAINING VINYL ETHER

FIELD OF THE INVENTION

This invention relates to electron donor compounds containing a vinyl ether group and to curable adhesive compositions containing those electron donor compounds.

BACKGROUND OF THE INVENTION

Adhesive compositions, particularly conductive adhesives, are used for a variety of purposes in the fabrication and assembly of semiconductor packages and microelectronic devices. The more prominent uses are the bonding of integrated circuit chips to lead frames or other substrates, and the bonding of circuit packages or assemblies to printed wire boards.

There exist electron acceptor/donor adhesives for use in low modulus adhesives, particularly in fast-cure adhesives for die attach applications in which vinyl ethers are the electron donors. However, the number of suitable vinyl ethers as donors is limited due to their low boiling points, high volatility, and difficult preparations. Thus, there is a need for the development of new electron donors for use in adhesives applications.

SUMMARY OF THE INVENTION

This invention relates to hybrid electron donor compounds comprising a vinyl ether and a carbon to carbon double bond external to an aromatic ring and conjugated with the unsaturation in the aromatic ring attached to a molecular (small molecule) or polymeric group. The presence of the vinyl ether group provides lower viscosity to these compounds compared to electron donor compounds that do not have the vinyl ether group; using a difunctional hybrid electron donor compound as an example, the hybrid will have a lower viscosity than the corresponding difunctional electron donor compound having the same electron donor group as each functionality.

The activity of the electron donor functionality other than the vinyl ether group can be increased by adding electron donating substituents on the aromatic ring, or decreased by adding electron withdrawing substituents. The activity can also be varied by steric interaction. An increase in the number or size of alkyl substituents on the carbon to carbon double bond will decrease the reactivity. Preferably, any substituents on the carbon to carbon double bond will be hydrogen, or will be hydrogen with a methyl group as the only other substituent.

Each electron donor group of the hybrid is linked to the molecular or polymeric entity through a linking group that is the product of the reaction between a functionality on the electron donor group and a co-reactive functionality on the molecular or polymeric group. Alternatively, the electron donor group may be attached to the molecular or polymeric group through a coupling reaction in which the carbon to carbon double bond external to the aromatic ring (of the electron donor) is formed during the reaction.

The molecular or polymeric group may be a cyclic, branched or linear alkyl, a siloxane or polysiloxane, a $C_1$ to $C_4$ alkoxy-terminated siloxane or polysiloxane, a polyether, a polyester, a polyurethane, a (poly)butadiene, or an aromatic, polyaromatic, or heteroaromatic group.

This invention is also a curable composition comprising one or more of the inventive electron donor compounds, and optionally a curing agent and one or more fillers.

This invention is also a curable composition comprising one or more of the inventive electron donor compounds and one or more co-polymerizable electron acceptor compounds, and may contain a curing agent and one or more fillers. Suitable electron acceptor compounds for co-polymerization are fumarates and maleates, for example, dioctyl maleate, dibutyl maleate, dioctyl fumarate, dibutyl fumarate. Resins or compounds containing acrylate and maleimide functionality are other suitable electron acceptor materials.

DETAILED DESCRIPTION OF THE INVENTION

The electron donor compounds of this invention will have one of the structures depicted here:

Structure I:

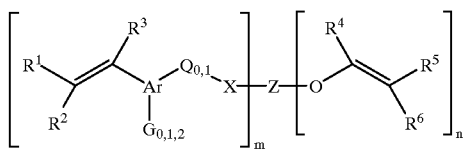

Structure II:

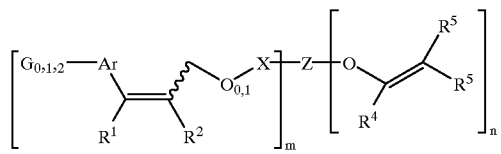

in which m and n are 1 to 6, preferably 1 to 3, and more preferably 1;

Ar is an aromatic or heteroaromatic ring having 3 to 10 carbon atoms within the ring, in which the heteroatoms may be N, O, or S;

$R^1$, $R^2$, and $R^3$ are independently hydrogen, Ar as described above, or an alkyl group having 1 to 12 carbon atoms; preferably $R^1$, $R^2$, and $R^3$ are hydrogen or an alkyl group having 1 to 4 carbon atoms, and more preferably are all hydrogen;

$R^4$, $R^5$, and $R^6$ are independently hydrogen, a methyl group or an ethyl group, and preferably two of $R^4$, $R^5$, and $R^6$ are hydrogen and one is methyl, and more preferably all are hydrogen;

G is —$OR^7$, —$SR^7$, —$N(R^1)(R^2)$, Ar as described above, or an alkyl group having 1 to 12 carbon atoms, in which $R^7$ is Ar as described above, or an alkyl group having 1 to 12 carbon atoms, preferably 1 to 4 carbon atoms, and $R^1$ and $R^2$ are as described above;

Q is an alkyl group having 1 to 12 carbon atoms;

X is

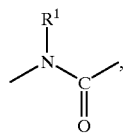 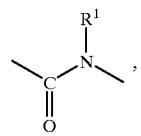

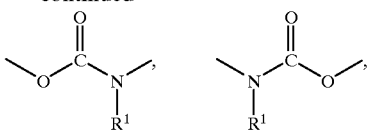

Z is an alkyl group, a siloxane, a polysiloxane, a $C_1$ to $C_4$ alkoxy-terminated siloxane or polysiloxane, a polyether, a polyester, a polyurethane, a (poly) butadiene, or an aromatic, polyaromatic, or heteroaromatic group. Materials for preparation as the Z group in these compounds are commercially available from a number of sources; for example, aromatic and polyaromatic materials may be obtained from BASF or Bayer; siloxanes and polysiloxanes from Gelest; polyethers from BASF; polyesters from Uniqema or Bayer; poly (butadiene)s from Elf-Atochem; polyurethanes from Bayer or BASF; and alkanes from Uniqema. Some of these sources will have available Z materials already functionalized for reaction with a co-reactive functionality on the vinyl ether or other electron donor starting material; in other cases, the practitioner will need to functionalize the materials in preparation for reaction with the electron donor containing starting material.

The Z groups may contain cyclic moieties or heteroatoms, and may contain pendant hydroxyl or thiol groups depending on the synthetic route for making the electron donor compound; for example, if one of the starting compounds contains a hydroxyl or thiol functionality that is reacted with an epoxy functionality, the Z group will contain a pendant hydroxyl or thiol group.

The exact composition or molecular weight of Z is not critical to the invention and can range widely depending on the requirements of the end use for the hybrid electron donor compound. The composition of Z can be chosen to give specific material properties in a final formulation, such as, rheological properties, hydrophilic or hydrophobic properties, toughness, strength, or flexibility. For example, a low level of crosslinking and free rotation about polymeric bonds will impart flexibility to a compound, and the presence of siloxane moieties will impart hydrophobicity and flexibility. The molecular weight and chain length will affect viscosity, the higher the molecular weight and the longer the chain length, the higher the viscosity.

As used in this specification, aromatic means a compound that meets the classical definition of an aromatic compound, that is, it contains cyclic clouds of delocalized $\pi$ electrons above and below the plane of the molecule and the $\pi$ clouds have a total of $(4n+2)$ electrons.

The aromatic group may contain an electron withdrawing group such as a nitro group, should less reactivity be desired, but in general, the compounds will have more practical utility in end use applications with greater reactivity.

These hybrid electron donor compounds can be prepared through standard addition or condensation reactions between a functionality on the starting material containing the electron donor group and a co-reactive functionality on the starting material containing the molecular or polymeric group and the vinyl ether functionality, or through coupling reactions using standard Wittig, Heck, or Stille methodologies. For example, useful starting compounds for the electron donor group (other than the vinyl ether) are cinnamyl alcohol or chloride and 3-isopropenyl-α,α-dimethylbenzylisocyanate. Although one skilled in the art can devise suitable variations in reactions by choice and location of functionality, the variations will be guided in practice by the commercial availability of starting materials or ease of synthetic routes.

Representative synthetic routes include:
1. the reaction of isocyanate functionality with (i) hydroxyl; or (ii) amine; or (iii) thiol functionality to create a carbamate, urea or thiocarbamate linkage, respectively;
2. the substitution of a halogen with (i) hydroxyl; or (ii) amine; or (iii) thiol functionality to create an ether, amine or thio-ether linkage, respectively;
3. the reaction of an epoxy functionality with (i) hydroxyl; or (ii) amine; or (iii) thiol functionality to create an ether, amine or thio-ether linkage, respectively.

These hybrid electron donor compounds can be blended with electron acceptor compounds, such as fumarates, maleates, acrylates, and maleimides, for co-polymerization to form cured adhesive compositions for use in a wide variety of applications. Suitable fumarates and maleates are, for example, dioctyl maleate, dibutyl maleate, dioctyl fumarate, dibutyl fumarate. Suitable acrylates are numerous and are commercially available, for example, from Sartomer. Suitable maleimides are easily prepared, for example, according to procedures described in U.S. Pat. Nos. 6,034,194 and 6,034,195 to Dershem.

The electron donor compounds can be formulated into adhesive, coating, potting or encapsulant compositions that are well suited for use in electronics applications. The formulations preferably will contain one or more curing agents and conductive or nonconductive fillers, and may also contain stabilizing compounds, adhesion promoters or coupling agents.

Exemplary curing agents are thermal initiators and photoinitiators, present in an amount of 0.1% to 10%, preferably 0.1% to 3.0%, by weight of the electron donor compound. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable; for example, the curing process can be started by irradiation, and in a later processing step curing can be completed by the application of heat to accomplish the thermal cure.

In general, these compositions will cure within a temperature range of 70° C. to 250° C., and curing will be effected at a temperature within the range of ten seconds to three hours. The time and temperature curing profile of each formulation will vary with the specific electron donor compound and the other components of the formulation, but the parameters of a curing profile can be determined by a practitioner skilled in the art without undue experimentation.

Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. When present, fillers will be in amounts of 20% to 90% by weight of the formulation.

Suitable adhesion promoters or coupling agents are silanes, silicate esters, metal acrylates or methacrylates, titanates, and compounds containing a chelating ligand, such as phosphine, mercaptan, and acetoacetate. When present, coupling agents will be in amounts up to 10% by weight, and preferably in amounts of 0.1% to 3.0% percent by weight of the hybrid electron donor compounds.

In addition, the formulations may contain compounds that lend additional flexibility and toughness to the resultant cured material. Such compounds may be any thermoset or thermoplastic material having a Tg of 150° C. or less, and typically will be a polymeric material, such as, a polyacrylate, poly(butadiene), polyTHF (polymerized tetrahydrofuran), carboxy-terminated butyronitrile rubber and polypropylene glycol. When present, these compounds may be in an amount up to about 15% by weight of the hybrid electron donor compound.

EXAMPLES

The following examples show representative hybrid electron donor compounds and reactions for their preparation. The electron donor reaction products were characterized by $^1$H-NMR and FT-IR spectroscopies. The examples are illustrative of the invention and are not intended as a limitation.

In these examples, fnc-$C_{36}$-fnc represents a mixture of isomers resulting from the dimerization of oleic and linoleic acids followed by conversion to the appropriate functionality in which fnc is —OH for alcohols, —NH$_2$ for amines, and —NCO for isocyanates; and

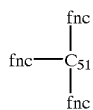

represents a mixture of isomers resulting from the trimerization of oleic and linoleic acids followed by conversion to the appropriate functionality in which fnc is —COOH for carboxyl groups, —CH$_2$OH for alcohols.

EXAMPLE 1

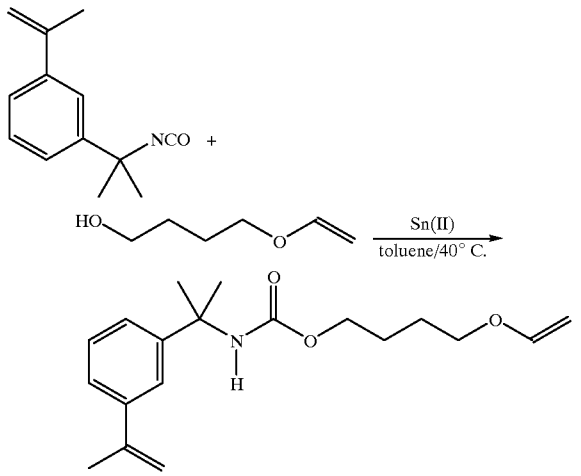

3-Isopropenyl-α,α-dimethylbenzyl isocyanate (103.96 g, 0.517 mole) was solvated in toluene (150 mL) in a 1,000 mL three-necked flask equipped with a mechanical stirrer, addition funnel and nitrogen inlet/outlet. The reaction was placed under nitrogen, and dibutyltin dilaurate (0.033 g) was added with stirring as the solution was heated to 40° C. The addition funnel was charged with 1,4-butanediol vinyl ether (60 g, 0.517 mole) dissolved in toluene (50 mL). This solution was added to the isocyanate solution over ten minutes, and the resulting mixture heated for an additional three hours at 40° C. After the reaction was allowed to cool to room temperature, the mixture was washed with distilled water three times. The isolated organic layer was dried over MgSO$_4$, filtered and the solvent removed in vacuo to give the product in 94% yield.

EXAMPLE 2

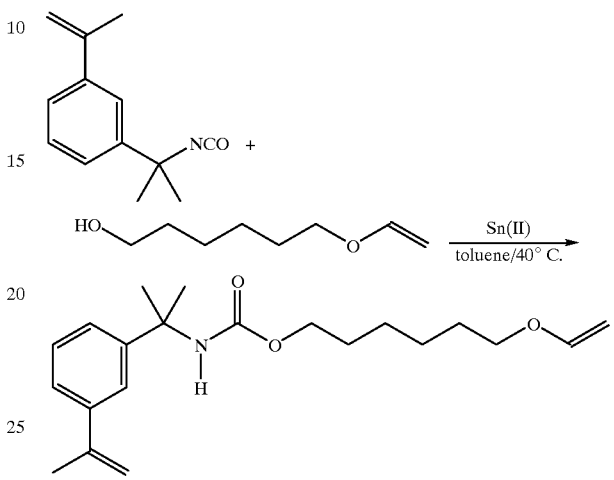

3-Isopropenyl-α,α-dimethylbenzyl isocyanate (38.06 g, 0.189 mole) was solvated in toluene (100 mL) in a 500 mL three-necked flask equipped with a mechanical stirrer, addition funnel and nitrogen inlet/outlet. The reaction was placed under nitrogen, and dibutyltin dilaurate (0.033 g) was added with stirring as the solution was heated to 40° C. The addition funnel was charged with 1, 6-hexanediol vinyl ether (27.27 g, 0.189 mole) dissolved in toluene (50 mL). This solution was added to the isocyanate solution over ten minutes, and the resulting mixture heated for an additional three hours at 40° C. After the reaction was allowed to cool to room temperature, the mixture was washed with distilled water three times. The isolated organic layer was dried over MgSO$_4$, filtered and the solvent removed in vacuo to give the product in 95% yield.

EXAMPLE 3

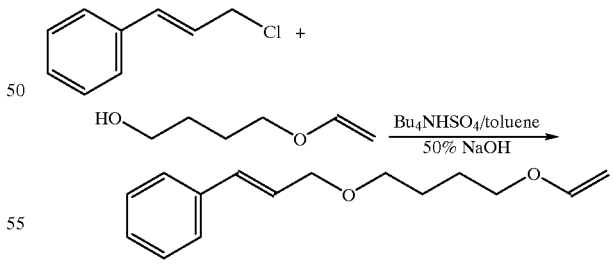

1,4-Butanediol vinyl ether (40.0 g, 0.344 mole), 50% NaOH (300 mL), tetrabutyl ammonium hydrogen sulfate (50.0 g, 0.148 mole), and cinnamyl chloride (52.56 g, 0.344 mole) in toluene was stirred for five hours at 53° C., 15 hours at 75° C. The reaction was allowed to cool to room temperature and the organic layer extracted and washed with brine three times. The isolated organic layer was dried over MgSO$_4$, filtered and the solvent removed in vacuo to give the product in 95% yield.

EXAMPLE 4

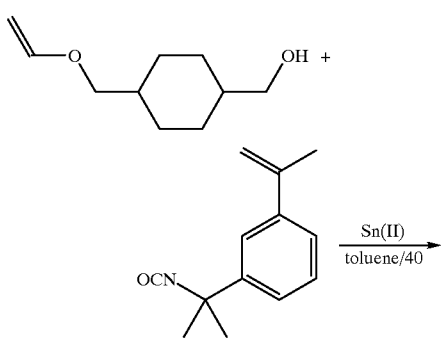

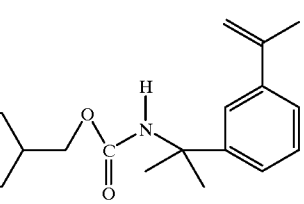

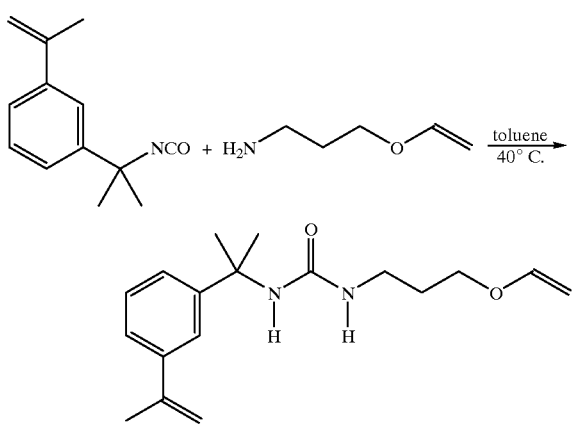

3-Isopropyl-α,α-dimethylbenzyl isocyanate (59.11 g, 0.294 mole) was solvated in toluene (100 mL) in a 500 mL three-necked flask equipped with a mechanical stirrer, addition funnel and nitrogen inlet/outlet. The reaction was placed under nitrogen, and dibutyltin dilaurate (0.033 g) was added with stirring as the solution was heated to 40° C. The addition funnel was charged with cyclohexanedimethanol monovinyl ether (50.0 g, 0.294 mole) dissolved in toluene (50 mL). This solution was added to the isocyanate solution over ten minutes, and the resulting mixture heated for an additional three hours at 40° C. After the reaction was allowed to cool to room temperature, the mixture was washed with distilled water three times. The isolated organic layer was dried over $MgSO_4$, filtered and the solvent removed in vacuo to give the product in 97% yield..

EXAMPLE 5

One molar equivalent of 3-isopropenyl-α,α-dimethylbenzyl isocyanate is solvated in toluene in a three-necked flask equipped with a mechanical stirrer, addition funnel and nitrogen inlet/outlet. The reaction is placed under nitrogen and the addition funnel is charged with one molar equivalent of 3-amino-1-propanol vinyl ether dissolved in toluene. This solution is added to the isocyanate solution over ten minutes, and the resulting mixture heated for an additional three hours at 40° C. After the reaction is allowed to cool to room temperature, the mixture is washed with distilled water three times. The isolated organic layer is dried over $MgSO_4$, filtered and the solvent removed in vacuo to give the product.

EXAMPLE 6

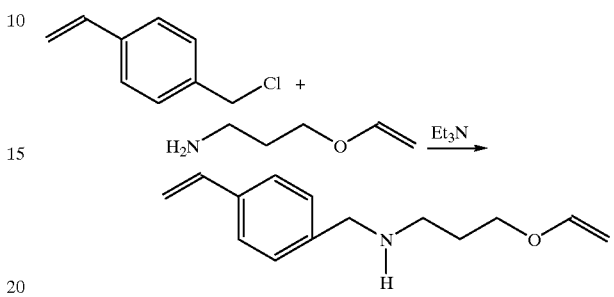

One molar equivalent of 3-amino-1-propanol vinyl ether and one molar equivalent of triethylamine are mixed in dry ethylene chloride at room temperature, to which is added one molar equivalent of 4-vinyl benzyl chloride in dry methylene chloride. The mixture is allowed to react for seven hours. The solvent is evaporated and the crude product is purified by column chromatography using a gradient of hexane/ethyl acetate.

EXAMPLE 7

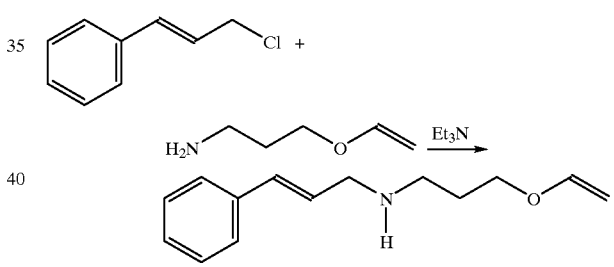

One molar equivalent of 3-amino-1-propanol vinyl ether and one molar equivalent of triethylamine are mixed in dry ethylene chloride at room temperature, to which is added one molar equivalent of cinnamyl chloride in dry methylene chloride. The mixture is allowed to react for seven hours. The solvent is evaporated and the crude product is purified by column chromatography using a gradient of hexane/ethyl acetate.

EXAMPLE 8

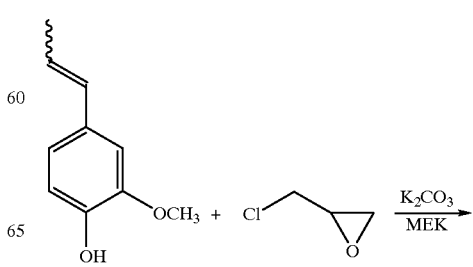

-continued

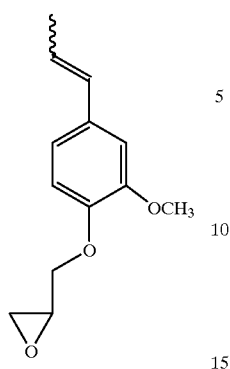

Isoeugenol (20 g, 0.12 mole), epichlorohydrin (33.8 g, 0.37 mole) and potassium carbonate (33.7 g, 0.244 mole) were solvated in methyl ethyl ketone (MEK) (100 mL) in a 500 mL three-necked flask equipped with a mechanical stirrer and nitrogen inlet/outlet. The reaction was placed under nitrogen, and was heated for five hours at 90° C. After the reaction was allowed to cool to room temperature, the salt was filtered and the filtrate was washed three times with 10% $Na_2SO_4$. The isolated organic layer was dried over $MgSO_4$, filtered, and the filtrate removed in vacuo to give the product.

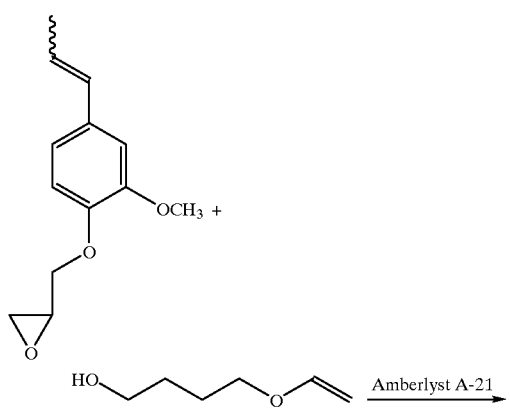

One molar equivalent of isoeugenol/epichlorohydrin adduct, one molar equivalent of 1,4-butanediol vinyl ether and catalytic amount of Amberlyst A-21 ion exchange resin are heated together at 90° C. for 20 hours. The Amberlyst resin is separated from the reaction mixture to give the product.

EXAMPLE 9

Other hybrid electron donor compounds can be made according to similar procedures. The following reaction schemes show other aromatic ring starting compounds and vinyl ether containing compounds with the resulting hybrid electron donor compounds.

EXAMPLE 9-A

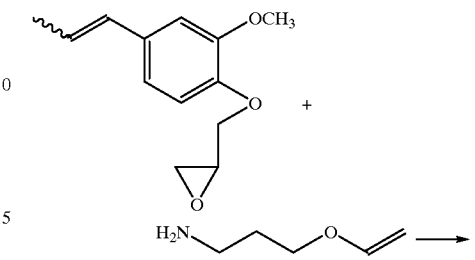

EXAMPLE 9-B

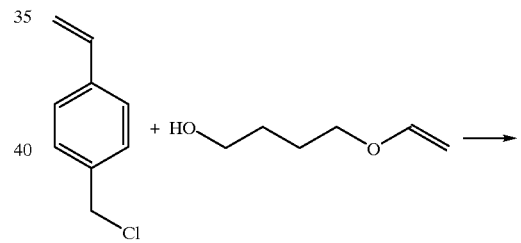

EXAMPLE 9-C

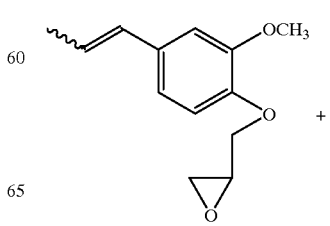

-continued
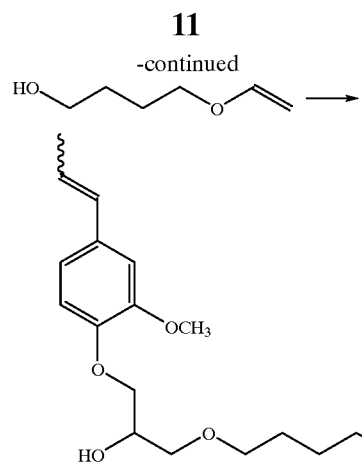
EXAMPLE 9-D
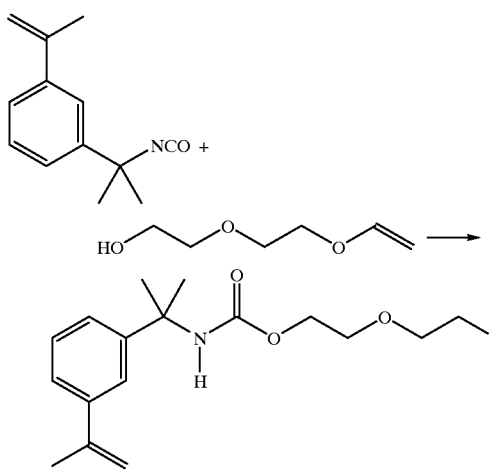
EXAMPLE 9-E
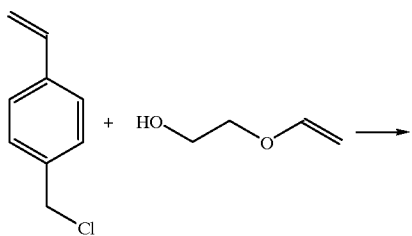
EXAMPLE 9-F
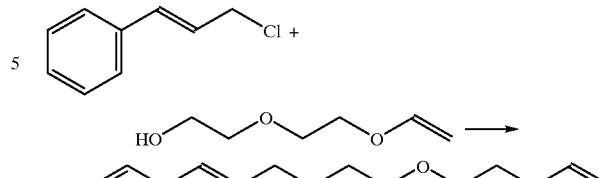
EXAMPLE 9-G
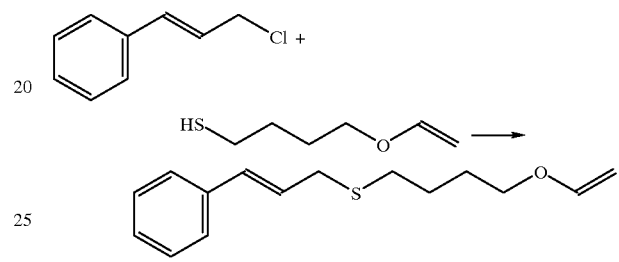
EXAMPLE 9-H
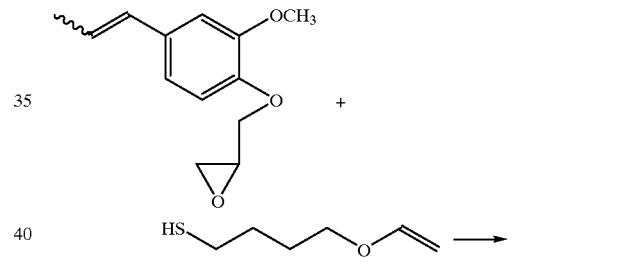
EXAMPLE 9-I
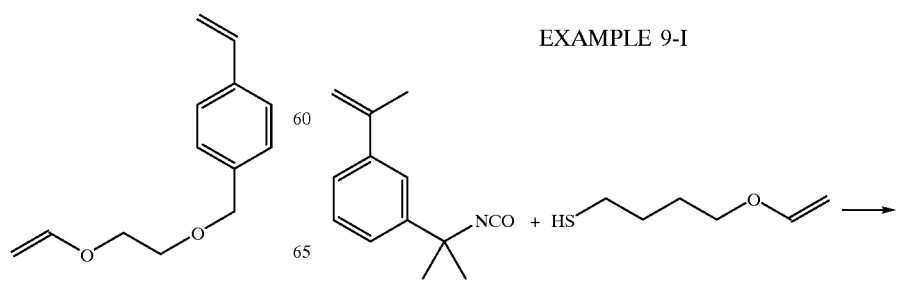

-continued
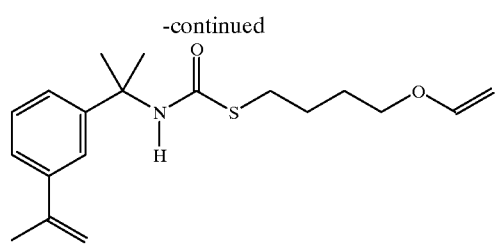
EXAMPLE 9-J
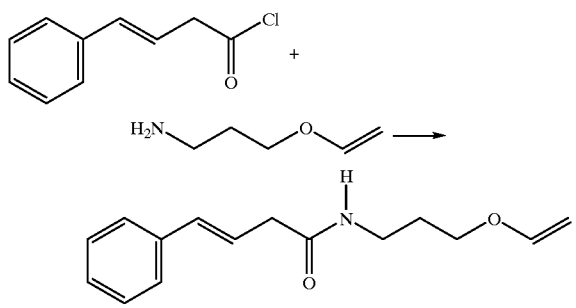
EXAMPLE 9-K
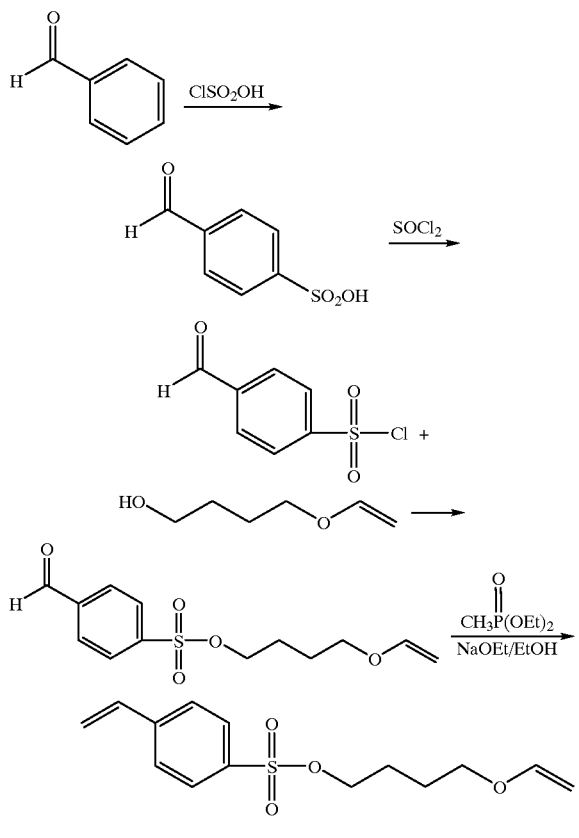
EXAMPLE 9-L
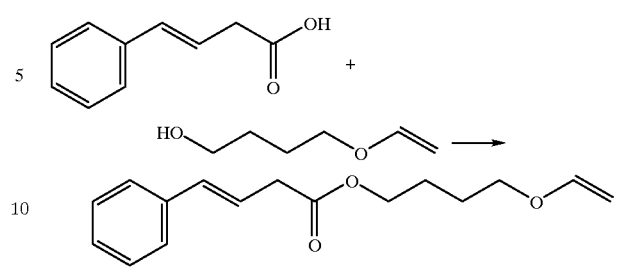
EXAMPLE 9-M
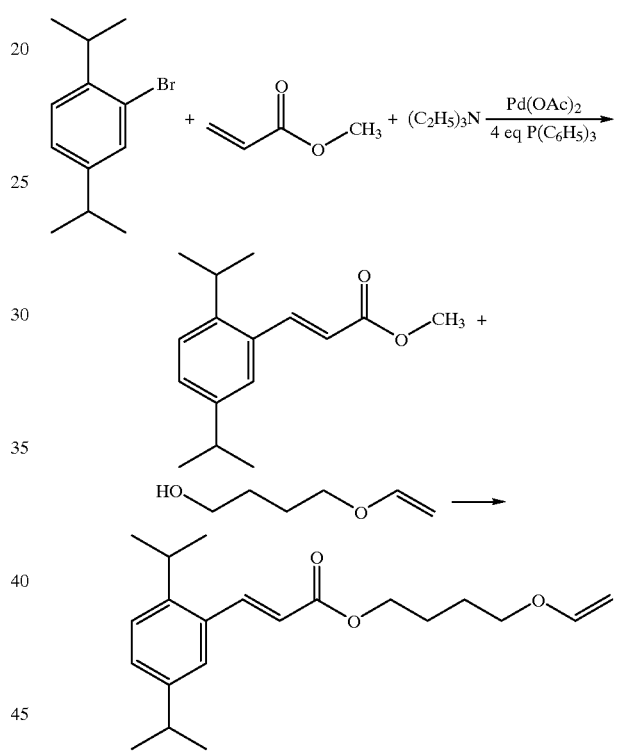
EXAMPLE 9-N
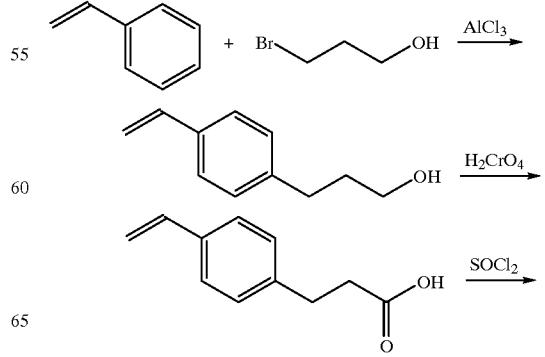

-continued

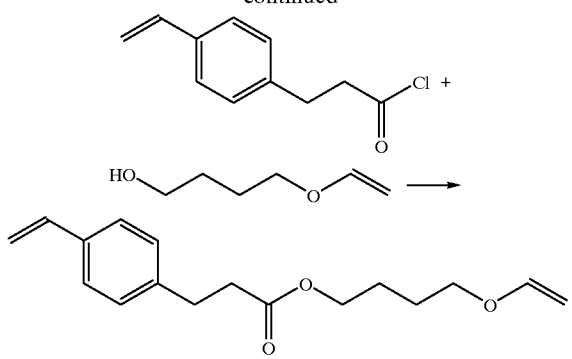

EXAMPLE 9-O

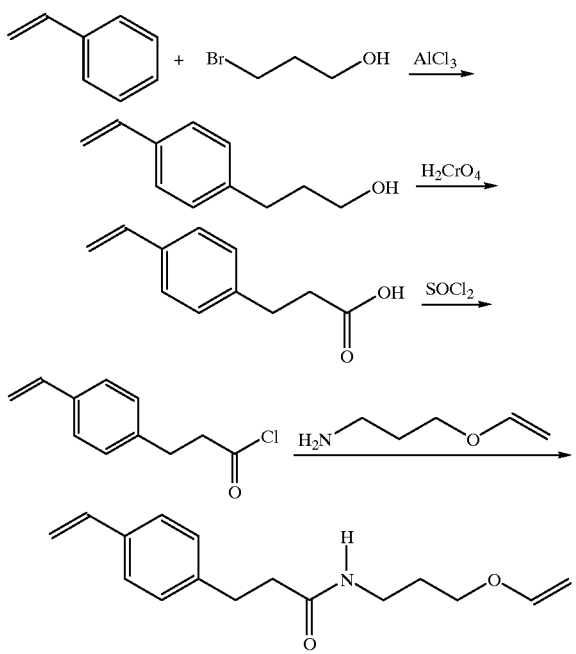

EXAMPLE 10

Adhesive Formulation

Three of the hybrid electron donor compounds from examples 1, 2, and 3 were formulated into adhesive compositions using a bismaleimide as the electron acceptor. The bismaleimide was derived from amino-terminated polyoxybutylenes (Versalink P650, Air Products) and maleic anhydride according to the procedures outlined in U.S. Pat. No. 4.745.197, using USP-MD (Witco Corporation) as an initiator.

These adhesive compositions were cured (copolymerization of the electron donor and the electron acceptor) using DSC. Exotherms for each of these resins appeared to be qualitatively similar in peak, and in peak to onset characteristics. The results are shown in the following table:

| Die attach paste with hybrid electron donor from | Onset (° C.) | Peak Temp (° C.) | Onset-to-Peak (° C.) | ΔH (J/g) |
|---|---|---|---|---|
| Example 1 | 97.22 | 112.14 | 14.92 | 286.2 |
| Example 2 | 92.97 | 107.15 | 14.8 | 254.5 |
| Example 3 | 103.04 | 126.88 | 23.84 | 325.8 |

The same three electron donors were formulated into die attach adhesive compositions and tested for die shear strength. The adhesives were placed between a leadframe (Pd, Ag, or Cu) and a 120×120 mil silicon die and cured on a hot plate at 200° C. for about 60 seconds. Pressure was applied to the side of the die at room temperature, and when the die and leadframe assembly was heated to 240° C., until shearing occurred. The formulations and results are reported in the tables below.

| Die Attach Formulation 1 ||
| Component | Mass (g) |
|---|---|
| BisMaleimide (Versalink P650) (electron acceptor) | 1.65 |
| Hybrid electron donor from example 1 | 0.50 |
| Maleic anhydride 8% (Ricon 131) (reactive diluent) | 0.25 |
| Initiator | 0.05 |
| Blend of adhesion promoters | 0.05 |
| Silver Flake | 5.51 |

| Room Temp Die Shear (Kg) | | | | Hot (240° C.) Die Shear (Kg) | | |
|---|---|---|---|---|---|---|
| Pd | Ag | Cu | leadframe | Pd | Ag | Cu |
| 18.0 | 12.0 | 17.0 | | 2.6 | 1.4 | 1.3 |

| Die Attach Formulation 2 ||
| Component | Mass (g) |
|---|---|
| BisMaleimide (Versalink P650) (electron acceptor) | 0.68 |
| Hybrid electron donor from example 2 | 0.50 |
| Maleic anhydride 8% (Ricon 131) (reactive diluent) | 0.14 |
| Initiator | 0.028 |
| Blend of adhesion promoters | 0.028 |
| Silver Flake | 4.13 |

| Room Temp Die Shear (Kg) | | | | Hot (240° C.) Die Shear (Kg) | | |
|---|---|---|---|---|---|---|
| Pd | Ag | Cu | leadframe | Pd | Ag | Cu |
| 16.0 | 19.0 | 16.0 | | 3.2 | 1.8 | 0.8 |

| Die Attach Formulation 3 | |
|---|---|
| Component | Mass (g) |
| BisMaleimide (Versalink P650) (electron acceptor) | 2.26 |
| Hybrid electron donor from example 3 | 0.50 |
| Maleic anhydride 8% (Ricon 131) (reactive diluent) | 0.32 |
| Initiator | 0.064 |
| Blend of adhesion promoters | 0.064 |
| Silver Flake | 9.63 |

| Room Temp Die Shear (Kg) | | | | Hot (240° C.) Die Shear (Kg) | | |
|---|---|---|---|---|---|---|
| Pd | Ag | Cu | leadframe | Pd | Ag | Cu |
| 7.1 | 7.4 | 5.6 | | 2.2 | 1.6 | 1.4 |

What is claimed is:

1. A compound having the structure:

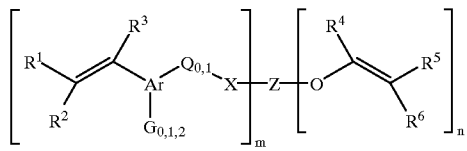

in which m and n are independently 1 to 6;

Ar is an aromatic or heteroaromatic ring having 3 to 10 carbon atoms within the ring, in which the heteroatom is N, O, or S;

$R^1$, $R^2$, and $R^3$ are independently hydrogen, Ar as described above, or an alkyl group having 1 to 12 carbon atoms;

$R^4$, $R^5$, and $R^6$ are independently hydrogen, a methyl group or an ethyl group;

G is —$OR^7$, —$SR^7$, —$N(R^1)(R^2)$, Ar as described above, or an alkyl group having 1 to 12 carbon atoms, in which $R^7$ is Ar as described above, or an alkyl group having 1 to 12 carbon atoms, and $R^1$ and $R^2$ are as described above;

Q is an alkyl group having 1 to 12 carbon atoms;

X is

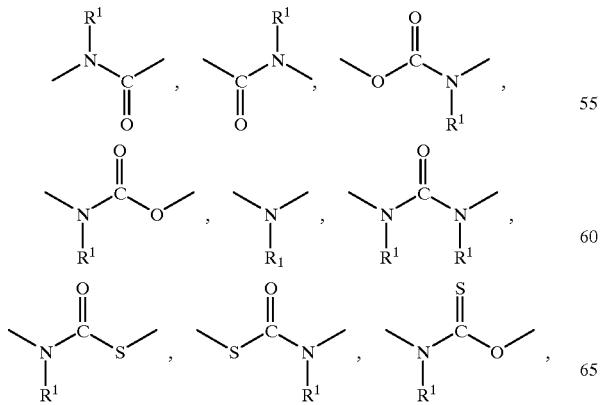

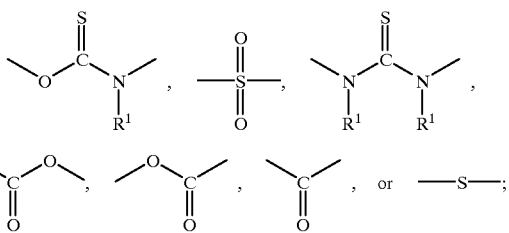

and

Z is an alkyl group, a siloxane, a polysiloxane, a $C_1$ to $C_4$ alkoxy-terminated siloxane or polysiloxane, a polyester, a polyurethane, a (poly)butadiene or an aromatic, polyaromatic, or heteroaromatic group.

2. A compound according to claim 1 selected from the group of compounds having the structures:

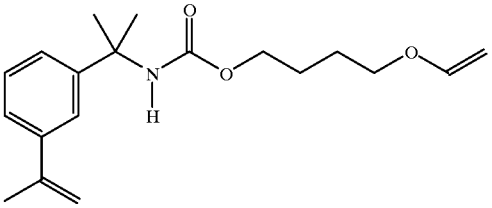

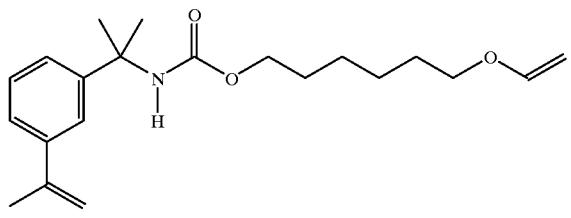

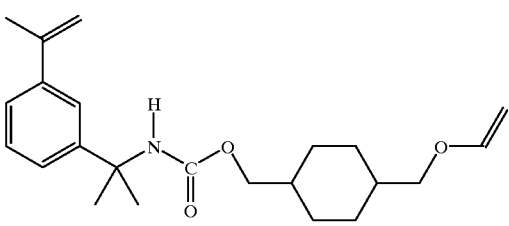

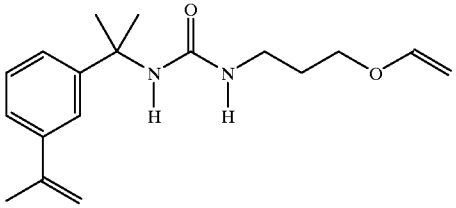

and

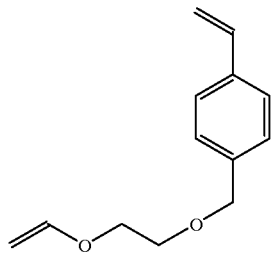

3. A compound having the structure:

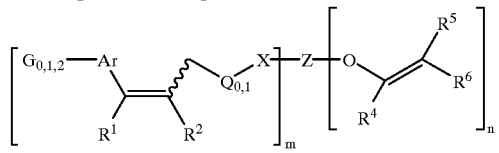

in which m and n are independently 1 to 6;

Ar is an aromatic or heteroaromatic ring having 3 to 10 carbon atoms within the ring, in which the heteroatom is N, O, or S;

$R^1$ and R2 are independently hydrogen, Ar as described above, or an alkyl group having 1 to 12 carbon atoms;

$R^4$, $R^5$, and $R^6$ are independently hydrogen, a methyl group or an ethyl group, G is —$OR^7$, —$SR^7$, —$N(R^1)(R^2)$, Ar as described above, or an alkyl group having 1 to 12 carbon atoms, in which $R^7$ is Ar as described above, or an alkyl group having 1 to 12 carbon atoms, and $R^1$ and $R^2$ are as described above;

Q is an alkyl group having 1 to 12 carbon atoms;

X is

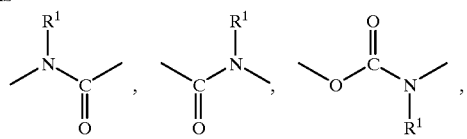

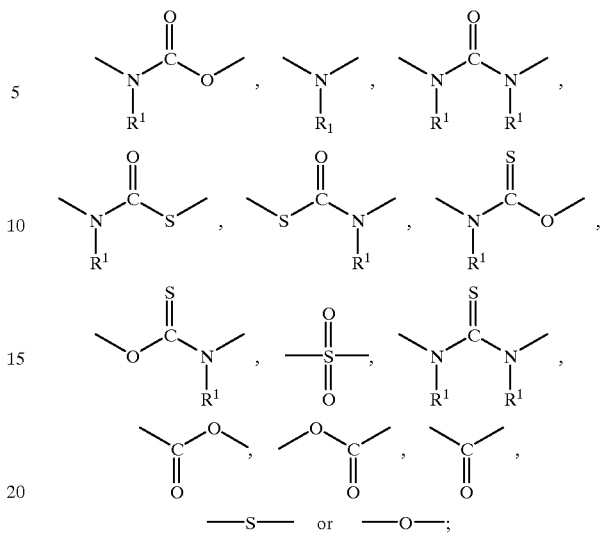

and

Z is an alkyl group, a siloxane, a polysiloxane, a $C_1$ to $C_4$ alkoxy-terminated siloxane or polysiloxane, a polyether, a polyester, a polyurethane, a (poly) butadiene or an aromatic, polyaromatic, or heteroaromatic group.

4. A compound according to claim 3 having the structure:

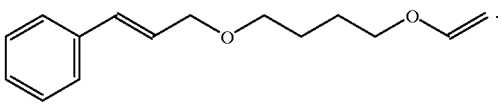

* * * * *